(12) United States Patent
Trokel

(10) Patent No.: US 11,534,083 B2
(45) Date of Patent: Dec. 27, 2022

(54) APPARATUS AND USE THEREOF FOR ANATOMICAL MAPPING OF BUTTOCKS

(71) Applicant: Yan Trokel, New York, NY (US)

(72) Inventor: Yan Trokel, New York, NY (US)

(*) Notice: Subject to any disclaimer, the term of this patent is extended or adjusted under 35 U.S.C. 154(b) by 440 days.

(21) Appl. No.: 16/739,966

(22) Filed: Jan. 10, 2020

(65) Prior Publication Data

US 2021/0212598 A1    Jul. 15, 2021

(51) Int. Cl.
*A61B 5/107* (2006.01)
*G01B 3/02* (2020.01)
*G01B 5/02* (2006.01)

(52) U.S. Cl.
CPC .......... *A61B 5/1072* (2013.01); *A61B 5/107* (2013.01); *G01B 3/02* (2013.01); *G01B 5/02* (2013.01); *A61B 5/1075* (2013.01); *A61B 5/1077* (2013.01)

(58) Field of Classification Search
CPC ..... A61B 5/1072; A61B 5/107; A61B 5/1077; A61B 5/1075; A61B 5/103; A61B 5/1109; A61B 5/445; G01B 3/04; G01B 3/563; G01B 3/02; G01B 5/04; G01B 5/02
See application file for complete search history.

(56) References Cited

U.S. PATENT DOCUMENTS

2012/0302923 A1* 11/2012 Santiago ............. A61B 5/1072
                                                                600/587
2017/0367621 A1* 12/2017 Nghiem ............... A61B 5/1072

* cited by examiner

*Primary Examiner* — Amy He
(74) *Attorney, Agent, or Firm* — Norris McLaughlin, P.A.

(57) ABSTRACT

A guide apparatus in the form of two flexible strips marked with scales, arranged perpendicular and slidable with respect to each other is used for anatomical mapping and marking of buttocks, especially for the purpose of defining sites suitable for lateral injection of filler into the buttocks for the purpose of lifting the buttocks as a cosmetic objective.

3 Claims, 9 Drawing Sheets

APPARATUS AND USE THEREOF FOR ANATOMICAL MAPPING OF BUTTOCKS

BACKGROUND OF THE INVENTION

The present invention relates to an apparatus in the form of a flexible guide which is particularly useful for anatomical mapping. The invention also relates to use of the apparatus for the mapping. The mapping effected by the present invention is of buttocks and is particularly useful for assistance with cosmetic minimally invasive, non-surgical procedures performed on buttocks, such as injection of filler to effect lifting of buttocks.

SUMMARY OF THE INVENTION

A guide apparatus for anatomical mapping of buttocks according to the invention includes two rectangular strips which may be of substantially the same width, each sufficiently flexible to conform to buttocks contours. The same guide apparatus as disclosed in U.S. Pat. No. 10,058,270 may be used in the present invention. However, the arcuate edge 15 with marking 20 and the window 16 shown in FIGS. 1 and 2 of U.S. Pat. No. 10,058,270 may be eliminated as these are intended specifically for facial mapping.

The guide apparatus includes first and second rectangular strips. The second rectangular strip is mounted to the first rectangular strip angularly fixedly at right angles to the first strip and slidably only in lengthwise directions of the second strip.

In an exemplary embodiment in connection with which the present invention is described herein in detail, the first strip is 1⅛ inches wide and the second strip is 1¼ inches wide. Therefore, it may be said that the two strips are of substantially the same width.

The invention is primarily a method for anatomical mapping of a buttock of a subject with an apparatus comprising:

first and second rectangular strips of substantially a same width and each sufficiently flexible to conform to buttock contours and having rectilinear edges;

the second strip being mounted to the first strip angularly fixedly at right angles to the first strip and slidably only in lengthwise directions of the second strip;

the method comprising:

marking on a buttock of a subject a curvilinear outline of an upper extremity of tensed gluteus maximus of the subject, whereafter subsequent steps are performed with gluteal muscles relaxed;

setting the apparatus with a distance of about 6 inches from an end edge of the second strip to a side edge of the first strip which side edge is proximal to the end edge of the second strip;

arranging the apparatus in contact with and conforming with a buttock of a subject with the end edge of the second strip aligned with a midline of the dorsal side of the torso of the subject;

using the proximal side edge of the first strip as a guide, marking a vertical first line on the buttock downwards from proximate the marked outline of the upper extremity of the gluteal maximus;

setting the apparatus with a distance of about 7 inches, or about 6 inches if the subject is under 5'7", from the end edge of the second strip to the proximal side edge of the first strip;

arranging the apparatus in contact with and conforming with the buttock of the subject with the end edge of the second strip aligned with the first vertical line;

using the proximal side edge of the first strip as a guide, marking a vertical second line on the buttock downwards from proximate the marked outline of the upper extremity of the gluteal maximus;

with the apparatus in contact with and conforming with the buttock of the subject, using the other side edge of the first strip as a guide, marking a horizontal third line intersecting an apex of the buttock and perpendicular to and connecting the first and second lines;

arranging the apparatus in contact with and conforming with the buttock of the subject to guide marking of a fourth line parallel to the first and second lines and bisecting the third line and extending proximate to the marked outline of the upper extremity of the gluteal maximus; and arranging the apparatus in contact with and conforming with the buttock of the subject to guide marking of a fifth line parallel to the third line and bisecting the first line and perpendicular to and connecting the first and second lines, thereby to form quadrants extending upwards from the apex of the buttock to the upper extremity of the gluteus maximus, a perimeter of each of the quadrants defining entry locations for lateral injection of a filler into the quadrants.

Another aspect of the invention is first marking the midline of the dorsal side of the torso of the subject along the groove on the dorsal side extending upwards from the intergluteal cleft.

Yet another aspect of the invention is using one or more edges of the apparatus, marking on the buttock a triangle having the second line as a base and a point proximate the marked outline of the upper extremity of the gluteal maximus as an apex, arms of the triangle meeting at the apex defining additional entry locations for lateral injection of a filler into an area within the triangle.

The mapping apparatus of the invention is used as a guide for marking on each buttock over the portion of the gluteal muscles from the apex of the buttock to proximate an upper extremity of the gluteus maximus four quadrants as guides for lifting a buttock in a safer and more aesthetically pleasing way than in the prior art. In the prior art, fat, for example, may be injected orthogonally into the buttock overlying the gluteus maximus. The needle of the syringe may inadvertently be caused to penetrate the gluteus maximus, which contains blood vessels, creating a risk of embolisms which may even be fatal. The mapping of the present invention provides the demarcation of sites for lateral (i.e., substantially parallel to the skin) insertion of syringe needles into the deep subcutaneous fat between the deep gluteal fascia which overlies the gluteus maximus and the gluteal fascia which overlies the deep subcutaneous fat and underlies the superficial subcutaneous fat. A preferred filler is comprised of calcium hydroxyapatite microspheres (commercially available under the trademark RADSIESSE).

DETAILED DESCRIPTION OF THE INVENTION

Figure 1:
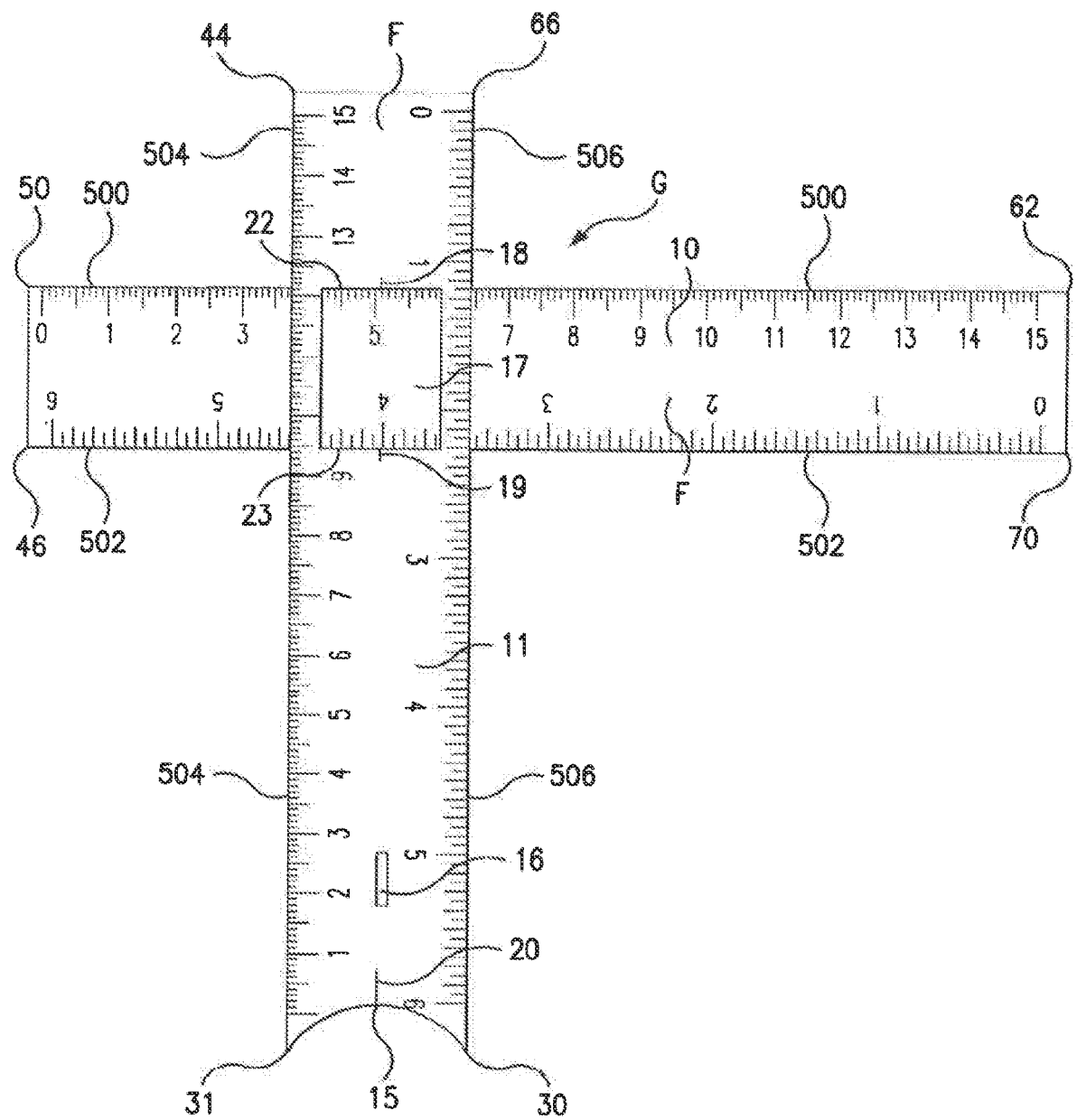
FIG. 1 is a plan view of the front face of a guide apparatus of the invention.
Figure 1A:
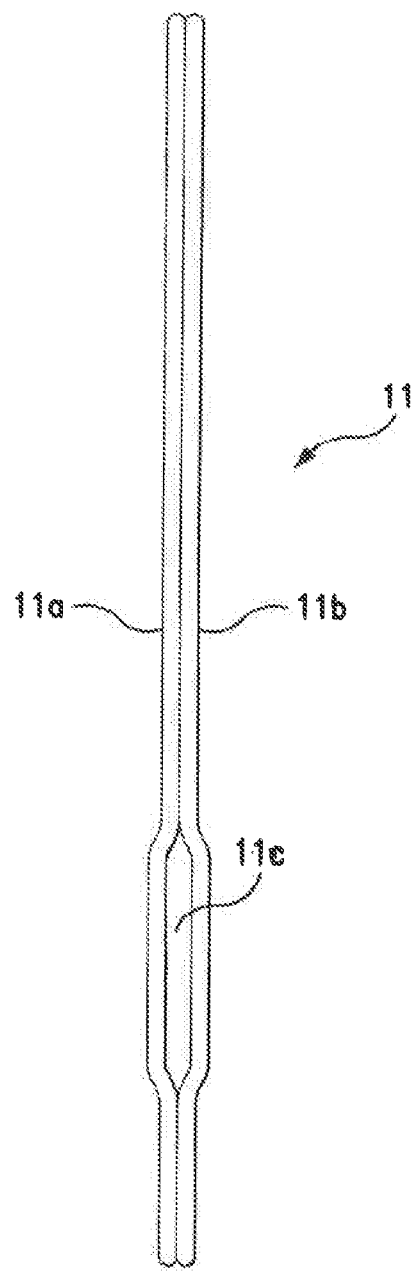
FIG. 1A is an edge view of one of the scripts comprising a guide apparatus.
Figure 2:
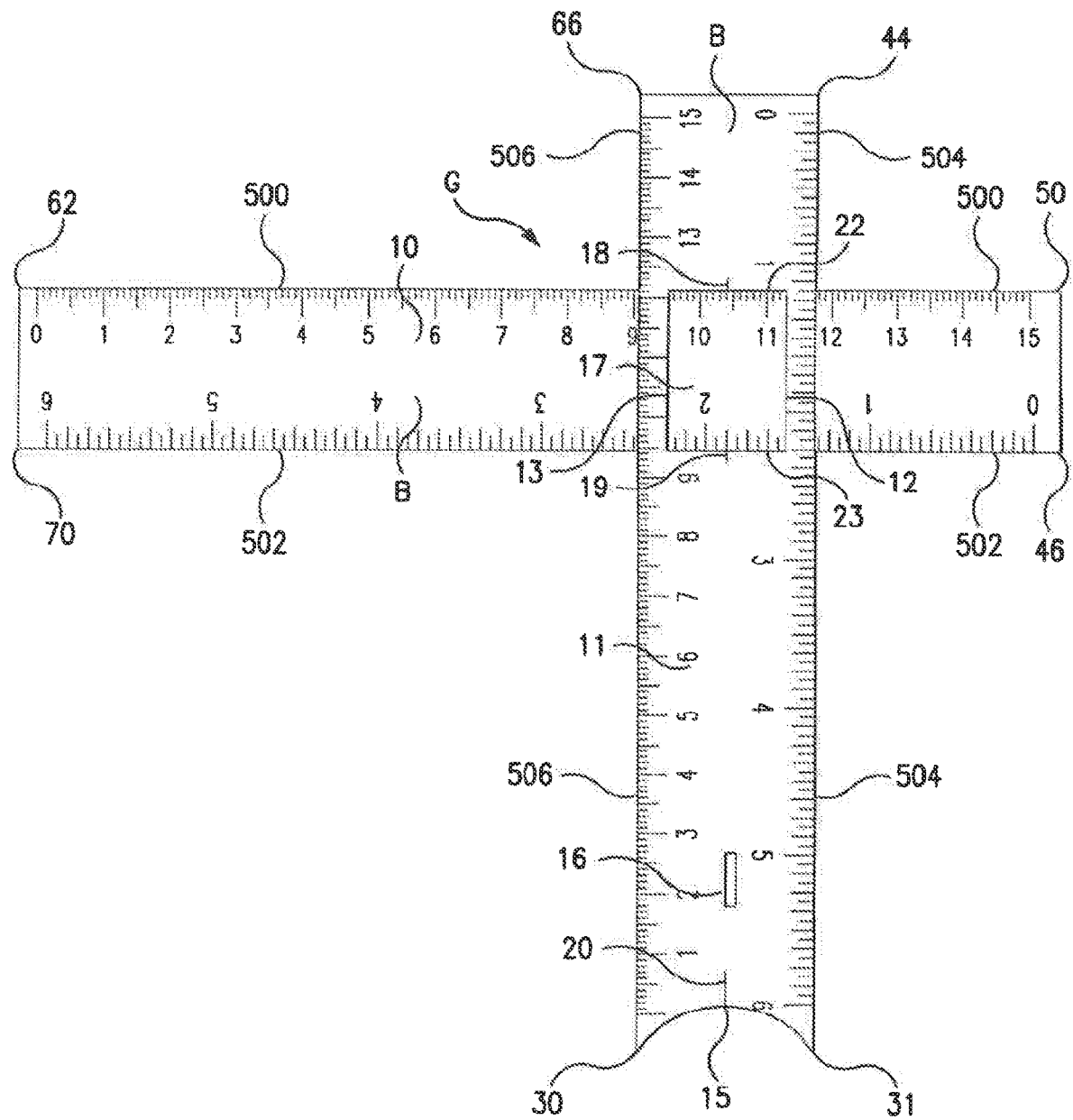
FIG. 2 is a plan view of the back face of a guide apparatus of the invention, it being understood that "front" and "back" are arbitrary and interchangeable.
Figure 3:
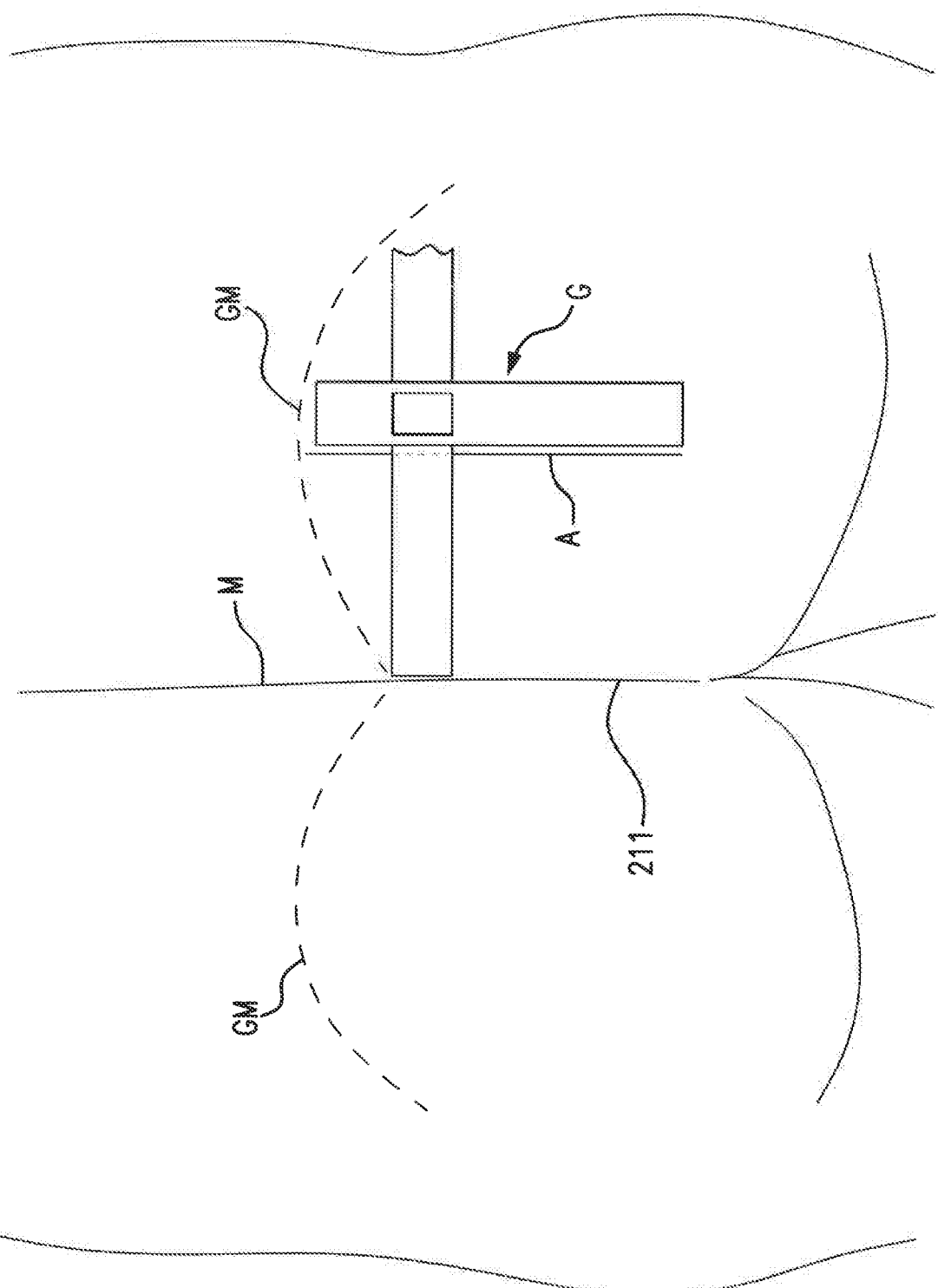
FIG. 3-8 is each a view of buttocks illustrating successive steps of the method of the invention.
Figure 4:
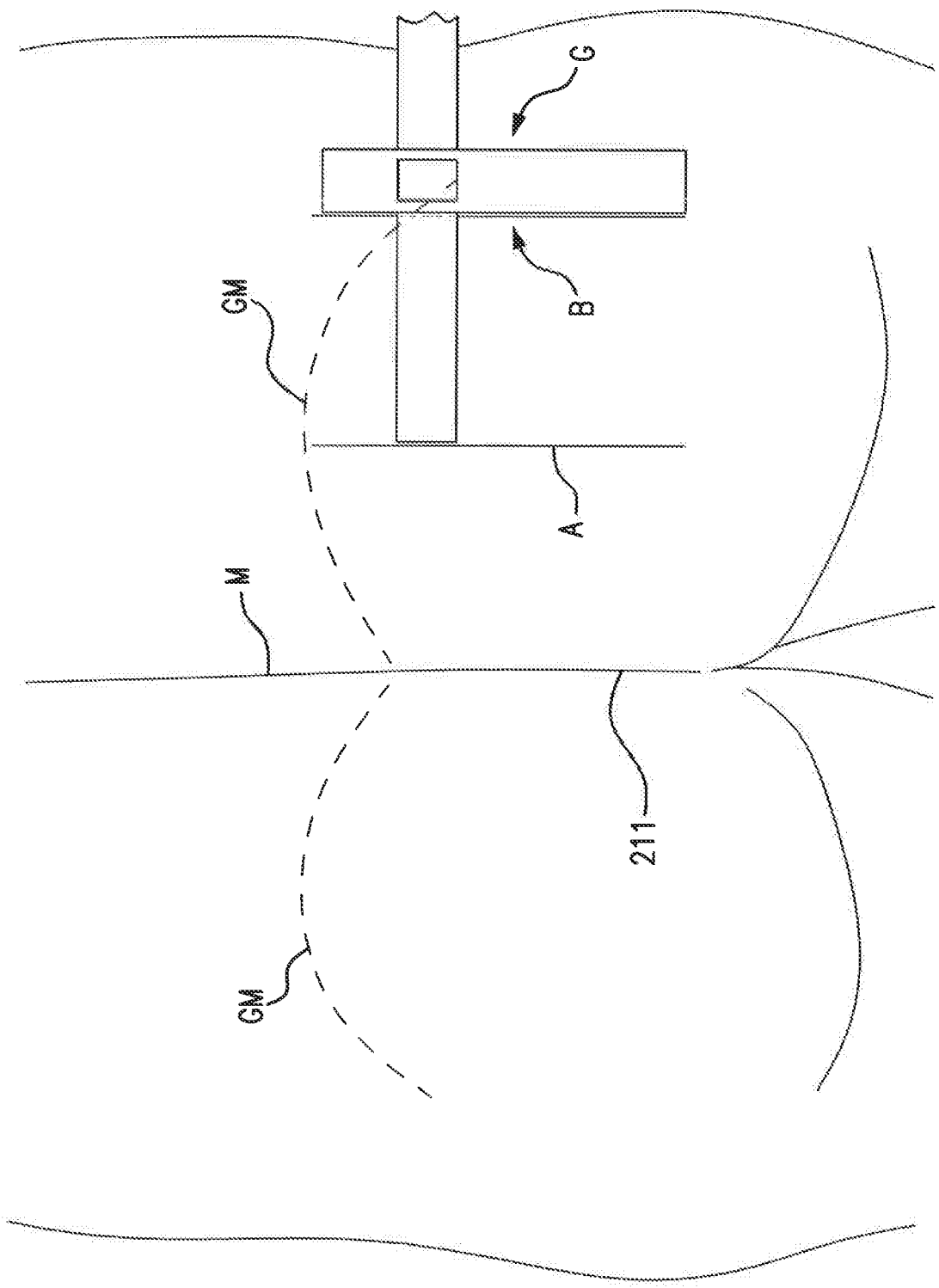
Figure 5:
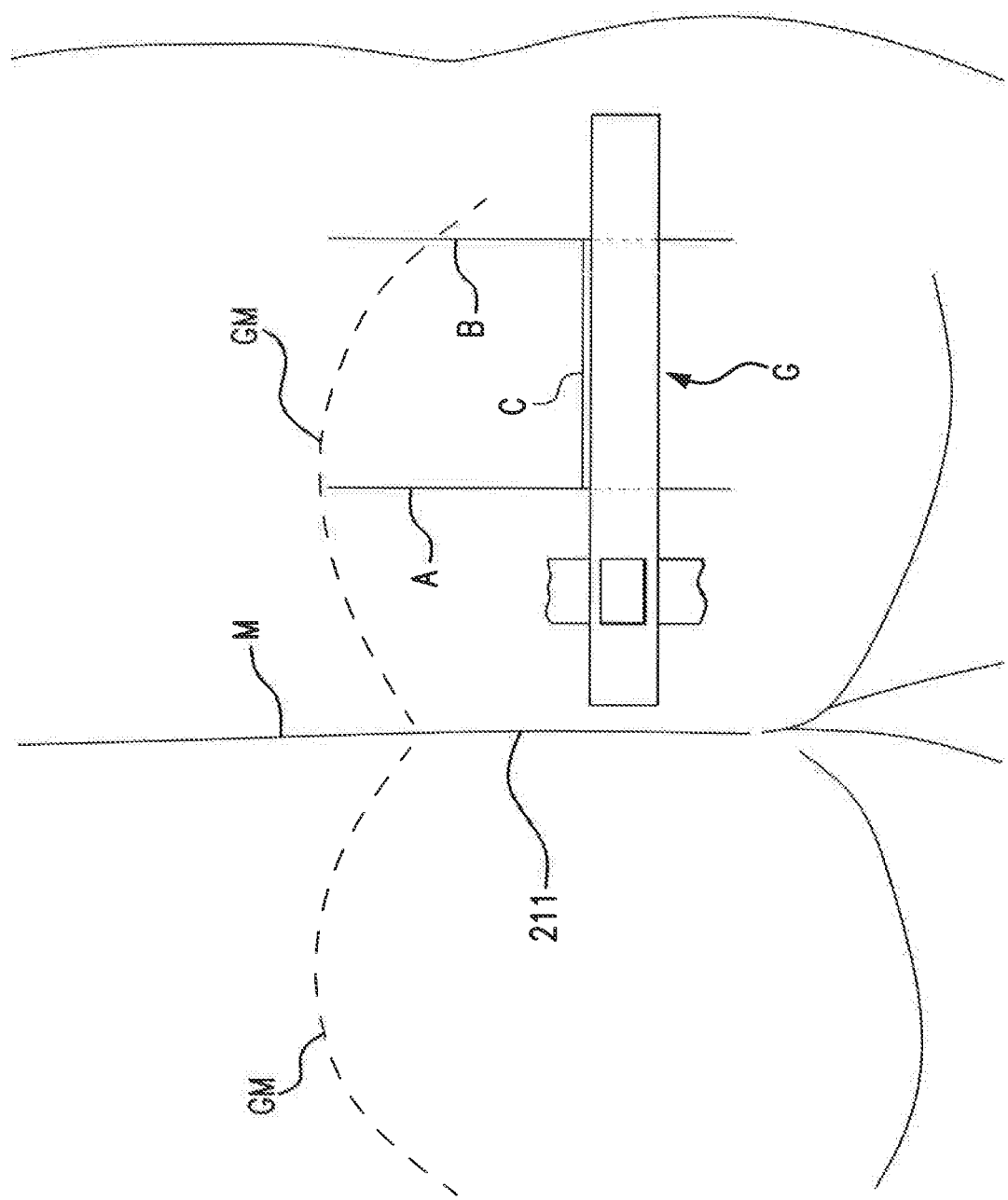
Figure 6:
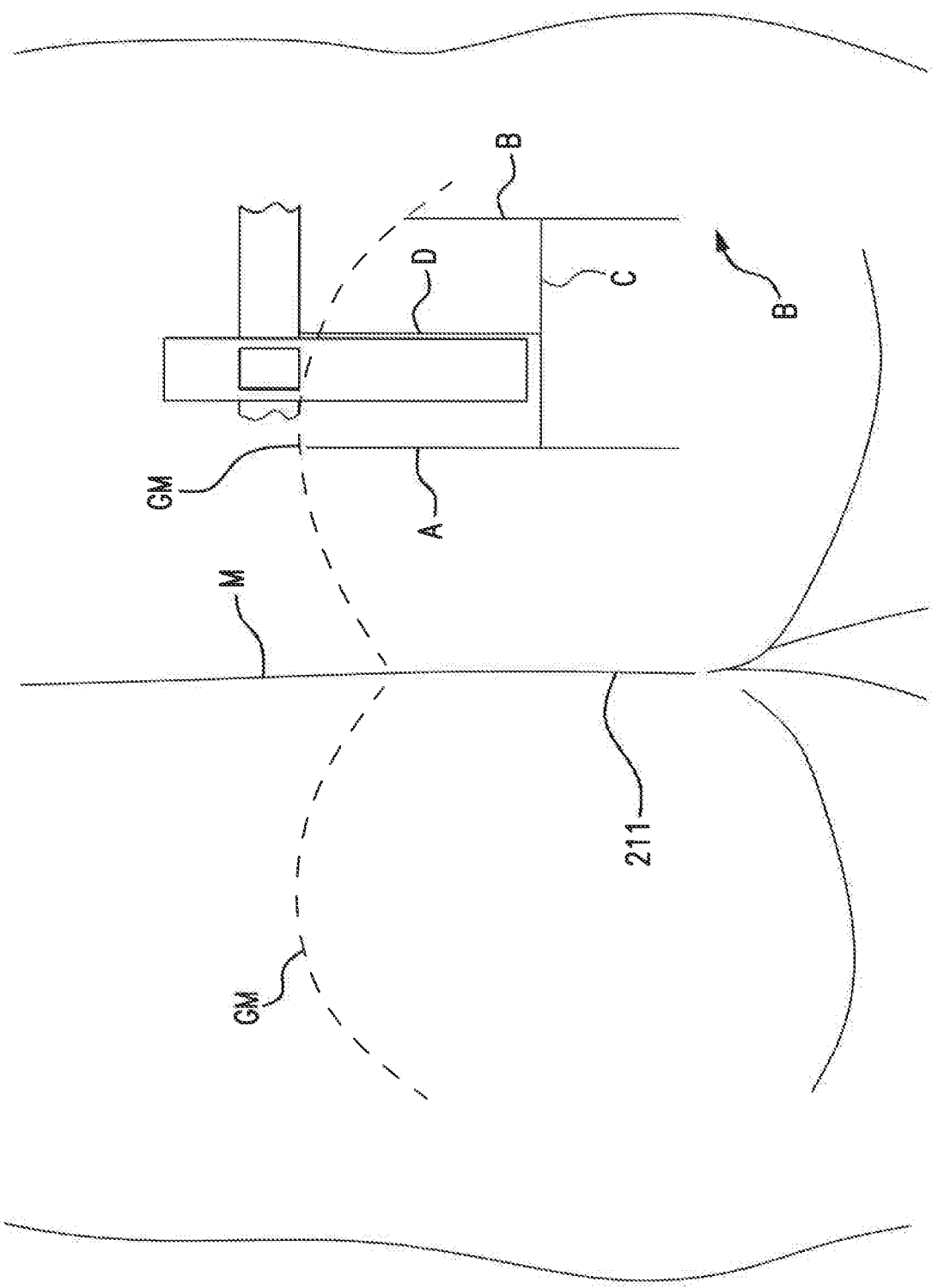
Figure 7:
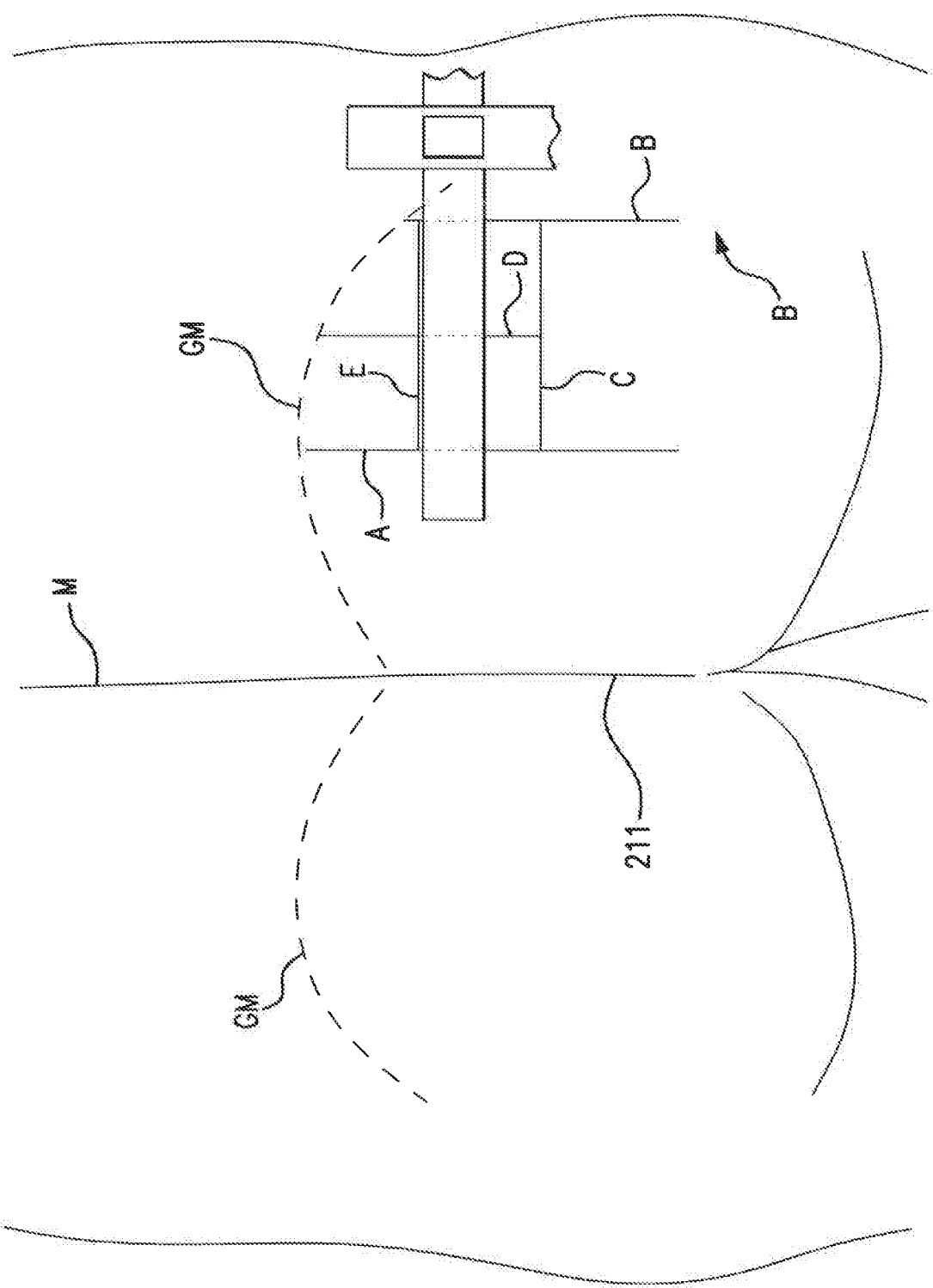

FIGS. 1 and 2 show front and back faces of an embodiment of a guide according to the invention for aiding a practitioner of cosmetic non-surgical procedures involving injections of fillers to locate appropriate injection sites (points, or zones or regions). The guide is constituted of a first flexible strip 11 and a second flexible strip 10 each preferably comprised of leather or natural or synthetic elastomer or of elastomeric or non-elastomeric plastic or of paper or cardboard, for example. The strips have parallel lengthwise edges 500, 502, 504 and 506. The strip 11 is comprised of two layers 11a and 11b (see FIG. 1A) which are fastened or adhered to each other (e.g., by stitching or by adhesive or by heat sealing), except for a length thereof slightly greater than the width of the strip 10 thereby forming a through passage 11c which receives the strip 10 therethrough. The strip 10 can be moved relative to the strip 11 by pulling on an end of the strip 10 to overcome friction between the strips 10 and 11 at their intersection, where they are in contact. Friction between the strips 10 and 11 prevents lengthwise displacement of the strip 10 relative to the strip 11 when neither end of the strip 10 is being pulled upon with sufficient force to overcome the aforementioned friction.

Numbers and markings are provided on both faces (front face F, back face B) of the strips 10 and 11 abutting each lengthwise edge of the strips 10 and 11. In the illustrated embodiment on each face of the strips 10 and 11 one edge is provided with a scale in centimeters and millimeters and the opposite edge is provided with a scale in inches and fractions thereof. Of course, these particular scales and that each edge has a scale different from the opposite edge are not requirements of the invention.

A rectangular window 17 is formed through the strip 11, where the through passage 11c is located. The window is essentially of the same dimension lengthwise of the strip 11 as the width of the strip 10 so that the scales at the edges 500, 502 of the strip 10, are visible on both faces F and B of the guide G. The window 17 is symmetrical with respect to an imaginary lengthwise center line on the strip 11. Top 22 and bottom 23 edges of the window 17 are immediately adjacent top and bottom edges of the strip 10 so that the scales adjacent both lengthwise edges of the strip 10 are visible through the window 17. The window is of sufficient width so that a number and the markings of the scales can be seen through the window. At the top and bottom edges 22, 23 of the window 17 on the imaginary lengthwise center line are inscribed lengthwise markings 18 and 19, respectively, on both faces. The identifications of parts numbers on FIGS. 1, 1A and 2 not referred to in the present description are incorporated herein by reference to the specification and drawings of U.S. Pat. No. 10,058,270, FIGS. 1, 1A and 2 of the present application being identical to the like identified figures of U.S. Pat. No. 10,058,270.

In the following written description and FIGS. 3-8 are described use of the flexible guide apparatus for mapping buttocks preparatory to a buttocks lift. Use of the guide is illustrated for one buttock. It is understood that the device is likewise used for the other buttock. When proceeding from one buttock to the other, the practitioner may find it convenient to simply flip over the guide apparatus so that it is a mirror image of its configuration when used on the first buttock. The guide is manipulated and held on the buttock by the practitioner. It is apparent that the practitioner will generally hold the guide in place with his/her fingertips. In order to provide unobstructed views, the practitioner's hands are not shown in the drawings. Also, in figures in which the guide is applied to a buttock, the guide is shown somewhat schematically for the sake of clarity of illustration. The numerical dimensions mentioned hereinbelow are based upon use of the guide apparatus on typical adult buttocks. The term "about" is defined herein as +/- (i.e., plus or minus) ½ inch.

As an optional step to provide a visual guide, continuation of a part of the midline M of the subject defined by the intergluteal cleft 211 is marked, with an edge of the apparatus G as a guide, along the groove on the dorsal side of the trunk of the subject, the midline continuing upwards from the intergluteal cleft 211. Then, the subject is instructed to tense up the gluteal muscles and the curvilinear upper periphery of the contracted gluteus maximus of each of the buttocks is marked with a respective curvilinear line GM. See FIG. 3. Subsequent mapping is performed with the buttocks in a relaxed condition.

The apparatus G is then set with a distance of 6 inches from an end edge 46-50 of the second strip 10 to a side edge 504 of the first strip 11. The apparatus G is arranged to be in contact with and conform with a buttock of the subject with the end edge 46-50 aligned with the midline M and a vertical line A extending downwards from approximately the line GM is marked on the buttock by means of the side edge 504 as a guide. See FIG. 3. (The line A is marked with the side edge 504 as a guide above and below the second strip 10 leaving a gap and the gap is closed by aligning any side edge of the apparatus G with the portions of the line A above and below the gap and marking to close the gap. Such procedure of filling in the gap is carried out in other of the steps as well and further description thereof is deemed unnecessary.)

The apparatus G is then set with the distance of 7 inches or, if the subject is under 5'7", 6 inches from the end edge 46-50 of the first strip 11 to the side of edge 504 of the second strip 10. The apparatus kG is arranged to be in contact and conform with the buttock with length of the second strip 10 perpendicular to the line A and with the intersection of the side edge 504 of the first strip 11 with the upper side edge 500 of the second strip 10 at the line GM; then, using the side edge 504 as a guide, a vertical line B is marked on the buttock downwards from the line GM. See FIG. 4.

The apparatus G is then used with the side edge 506 of the first strip 11 as a guide to mark a horizontal line C between and perpendicular to the lines A and B and intersecting the apex of the buttock, the apex being located visually. See FIG. 5.

Figure 8:
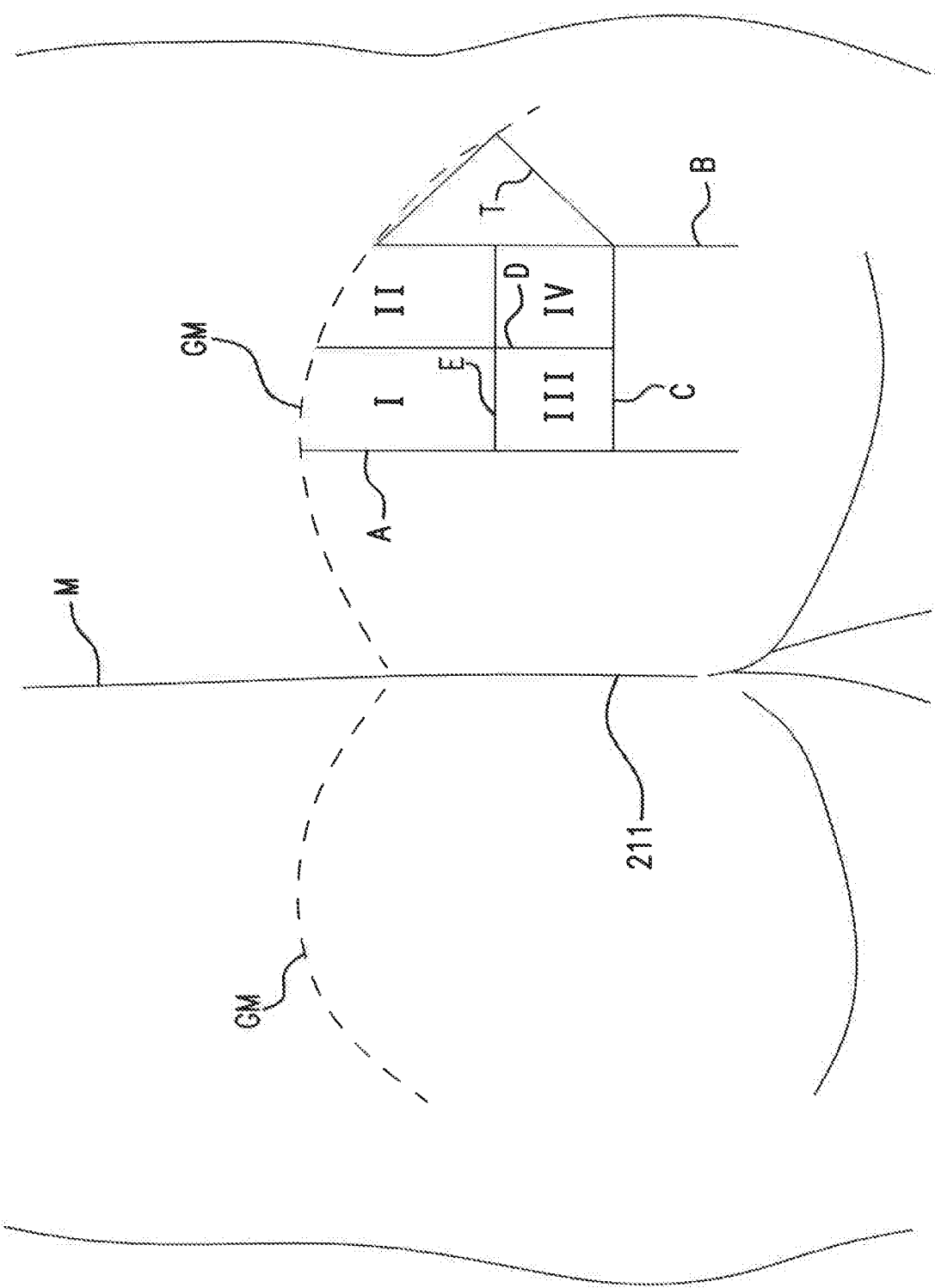

The apparatus G is then set to guide marking of a vertical line D parallel to lines A and B, bisecting line C (a bisect point being determined by measurement with any of the scales of the apparatus G) and extending downward from the line GM (FIG. 6) and to guide marking of a horizontal line E extending from line A to line B, perpendicular to lines A and B and bisecting line A (a bisect point being determined by measurement with any of the scales of the apparatus G). See FIG. 7. Thereby quadrants I, II, III and IV are formed (FIG. 8).

Similarly, the other buttock is mapped and marked, using the apparatus G flipped over in mirror image.

If the subject's buttock has any indentations on the lateral border, i.e., the side border remote from the intergluteal cleft 211, a triangle T may be projected from quadrants II and IV.

A purpose of the above described mapping and marking of the buttocks is to provide a map for a minimally invasive cosmetic procedure, namely, injection of a filler into each buttock to lift the buttocks and, if needed, to fill the aforementioned lateral indentations. Filler is injected laterally into the quadrants and, optionally, into the triangular regions T at sites at or proximate the borders of the quadrants and triangular regions, into the deep subcutaneous fat between the deep gluteal fascia which overlies the gluteus maximus and the gluteal fascia which overlies the deep subcutaneous fat and underlies the superficial subcutaneous fat.

The invention claimed is:

1. A method for anatomical mapping of a buttock of a subject with an apparatus comprising:

first and second rectangular strips of substantially a same width and each sufficiently flexible to conform to buttock contours and having rectilinear edges;

the second strip being mounted to the first strip angularly fixedly at right angles to the first strip and slidably only in lengthwise directions of the second strip;

the method comprising:

marking on a buttock of a subject a curvilinear outline of an upper extremity of tensed gluteus maximus of the subject, whereafter subsequent steps are performed with gluteal muscles relaxed;

setting the apparatus with a distance of about 6 inches from an end edge of the second strip to a side edge of the first strip which side edge is proximal to the end edge of the second strip;

arranging the apparatus in contact with and conforming with a buttock of a subject with the end edge of the second strip aligned with a midline of the dorsal side of the torso of the subject;

using the proximal side edge of the first strip as a guide, marking a vertical first line on the buttock downwards from proximate the marked outline of the upper extremity of the gluteal maximus;

setting the apparatus with a distance of about 7 inches, or about 6 inches if the subject is under 5'7", from the end edge of the second strip to the proximal side edge of the first strip;

arranging the apparatus in contact with and conforming with the buttock of the subject with the end edge of the second strip aligned with the first vertical line;

using the proximal side edge of the first strip as a guide, marking a vertical second line on the buttock downwards from proximate the marked outline of the upper extremity of the gluteal maximus;

with the apparatus in contact with and conforming with the buttock of the subject, using the other side edge of the first strip as a guide, marking a horizontal third line intersecting an apex of the buttock and perpendicular to and connecting the first and second lines;

arranging the apparatus in contact with and conforming with the buttock of the subject to guide marking of a fourth line parallel to the first and second lines and bisecting the third line and extending proximate to the marked outline of the upper extremity of the gluteal maximus; and arranging the apparatus in contact with and conforming with the buttock of the subject to guide marking of a fifth line parallel to the third line and bisecting the first line and perpendicular to and connecting the first and second lines, thereby to form quadrants extending upwards from the apex of the buttock to the upper extremity of the gluteus maximus, a perimeter of each of the quadrants defining entry locations for lateral injection of a filler into the quadrants.

2. The method according to claim 1, further comprising: first marking the midline of the dorsal side of the torso of the subject along the groove on the dorsal side extending upwards from the intergluteal cleft.

3. The method according to claim 1, further comprising using one or more edges of the apparatus, marking on the buttock a triangle having the second line as a base and a point proximate the marked outline of the upper extremity of the gluteal maximus as an apex, arms of the triangle meeting at the apex defining additional entry locations for lateral injection of a filler into an area within the triangle.

* * * * *